(12) United States Patent
Krishna et al.

(10) Patent No.: US 8,373,139 B2
(45) Date of Patent: Feb. 12, 2013

(54) OPTICAL LUMINESCENCE OF FUNCTIONALIZED FULLERENES IN AN OXYGEN FREE ENVIRONMENT

(75) Inventors: Vijay Krishna, Gainesville, FL (US); Brij M. Moudgil, Gainesville, FL (US); Benjamin L. Koopman, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 127 days.

(21) Appl. No.: 12/810,248

(22) PCT Filed: Jan. 5, 2009

(86) PCT No.: PCT/US2009/030120
§ 371 (c)(1),
(2), (4) Date: Sep. 13, 2010

(87) PCT Pub. No.: WO2009/089161
PCT Pub. Date: Jul. 16, 2009

(65) Prior Publication Data
US 2011/0012027 A1 Jan. 20, 2011

Related U.S. Application Data

(60) Provisional application No. 61/010,164, filed on Jan. 4, 2008.

(51) Int. Cl.
*G01N 21/64* (2006.01)
(52) U.S. Cl. .................................................. 250/459.1
(58) Field of Classification Search ............ 250/459.1
See application file for complete search history.

(56) References Cited

U.S. PATENT DOCUMENTS

| | | | | |
|---|---|---|---|---|
| 6,077,401 A * | 6/2000 | Fields et al. | ............ | 204/157.47 |
| 7,597,868 B2 * | 10/2009 | Senna et al. | ............ | 423/445 B |
| 2007/0003807 A1 | 1/2007 | Wudl et al. | | |
| 2007/0190384 A1 | 8/2007 | Tasaki et al. | | |

FOREIGN PATENT DOCUMENTS

| | | |
|---|---|---|
| JP | 11-262972 | 9/1999 |
| WO | WO 02-30816 | 4/2002 |

OTHER PUBLICATIONS

Bouchtalla et al., "[60]Fullerene immobilized in a thin functionalized polypyrrole film. Basic principles for the elaboration of an oxygen sensor," 2002, Materials Science and Engineering, vol. C 21, pp. 125-129.*

(Continued)

*Primary Examiner* — Kiho Kim
(74) *Attorney, Agent, or Firm* — Saliwanchik, Lloyd & Eisenschenk

(57) ABSTRACT

Functionalized fullerenes, when excited at any of a broad range of wavelengths in an oxygen free environment, undergo luminescence. The oxygen sensitive luminescence of functionalized fullerenes is used for numerous applications including oxygen detection; irradiation induced healing of polymeric materials; and phosphors for optical location and display applications. The degradation of the functionalized fullerenes allows for the detection of oxygen by diminished luminescence when the fullerenes are exposed to an irradiation source, such as a laser beam, in the presence of oxygen. The luminescence from a portion of a surface of a material with functionalized fullerenes allows for the location of the surface containing a functionalized fullerene target in the absence of oxygen or to heat the object in the area irradiated that is exposed to oxygen. The localized heating can be used to repair defects to a material containing the functionalized fullerenes. Materials containing functionalized fullerenes can be used as phosphors in display applications.

20 Claims, 3 Drawing Sheets

OTHER PUBLICATIONS

Nagl et al., "Optical sensing and imaging of trace oxygen with record response," 2007, Angewandte Chmie International Edition, Wiley-VcH Verglar Gambh & Co, vol. 46, pp. 2317-2319.*

Ajayan, P.M. et al., "Nanotubes in a Flash-Ignition and Reconstruction," *Science*, Apr. 26, 2002, p. 705, vol. 296.

Amao, Y. et al., "A novel optical oxygen sensing system based on triplet-triplet reflectance of fullerene $C_{60}$-polystyrene film by time-resolved spectroscopy using diffuse reflectance laser flash photolysis," *Analyst*, 2000, pp. 523-526, vol. 125.

Amao, Y. et al., "Fullerene $C_{60}$ immobilized in polymethylmethacrylate film as an optical temperature sensing material," *Analyst*, 2000, pp. 847-849, vol. 28.

Nagl, S. et al., "Optical Sensing and Imaging of Trace Oxygen with Record Response," *Angew. Chem. Int. Ed.*, 2007, pp. 2317-2319, vol. 46.

Krishna, V. et al., "Optical heating and rapid transformation of functionalized fullerenes," *Nature Nanotechnology*, May 2010, pp. 330-334, vol. 5, No. 5.

* cited by examiner

//www.w3.org/1998/Math/MathML
OPTICAL LUMINESCENCE OF FUNCTIONALIZED FULLERENES IN AN OXYGEN FREE ENVIRONMENT

CROSS-REFERENCE TO RELATED APPLICATION(S)

This application is the U.S. national stage application of International Patent Application No. PCT/US2009/030120, filed Jan. 5, 2009, which claims the benefit of U.S. Provisional Application Ser. No. 61/010,164, filed Jan. 4, 2008, the disclosures of which are hereby incorporated by reference in their entireties, including any figures, tables, or drawings.

The subject invention was made with government support under the National Science Foundation, Contract No. EEC9402989. The government has certain rights to this invention.

BACKGROUND OF THE INVENTION

A wide variety of physiological transformations, chemical reactions, and technical processes produce or consume $O_2$, while many anoxic species, numerous chemical syntheses, and manufacturing protocols demand its complete absence. The presence of $O_2$ in an extraterrestrial environment is used to indicate the potential for life forms. Hence, trace oxygen detection is important for many endeavors, including aerospace research, environmental safety and food storage.

Common trace oxygen sensors are based on amperometry (Clark electrodes). Although amperometry based instruments are sensitive and applicable over a wide temperature range, they are difficult to miniaturize, invasive, limited to discrete positions, and limited by the stability of the electrode surface and the oxygen diffusion barrier at the surface. To overcome such problems, attention has been directed to optical sensing methods based on luminescence quenching of an indicator by oxygen. Most optical oxygen sensors are based on the quenching of the long-lived luminescence exhibited by polycyclic aromatic hydrocarbons, transition-metal complexes, and metalloporphyrins. Typically, these compounds are placed in inert permeable polymer membranes.

The highest optical oxygen sensitivity has been achieved by detecting the quenching of the delayed fluorescence of fullerenes embedded in permeable polymeric films. The electronic states and transitions of fullerenes are near the interface between discrete molecular orbitals and band structures due to the large number of electrons in $\pi$ orbitals. The fluorescence of fullerenes, such as $C_{60}$ and $C_{70}$, is atypical in several ways and has been exploited to produce oxygen sensors that have sensitivities in the parts per billion range as reported in: Amao et al. ("Optical Sensor System Using Photofunctional Materials for Oxygen Pressure on Solid Surface." *Analyst* 2000, 125:523-6) where fluorescence decay was monitored at 740 nm; and Nagl et al. ("Optical Sensing and Imaging of Trace Oxygen with Record Response." *Angew. Chem, Int. Ed.* 2007, 46:2317-9) where emission was monitored at 650 to 710 nm. These sensors were determined to be stable over multiple (>100) light exposures in oxygen containing atmospheres with no disclosed degradation of the fullerenes.

However, the insolubility of fullerenes in many solvents has limited their application and production for uses such as oxygen detection sensor. New materials with good oxygen sensitivity while being environment friendly and easy to manipulate are highly desired.

BRIEF SUMMARY OF THE INVENTION

Embodiments of the invention provide a method of illumination by irradiating a material comprising functionalized fullerenes in an oxygen free environment. One embodiment involves a luminescent device which comprises a material comprising functionalized fullerenes and a source of radiation. Upon irradiation of the functionalized fullerenes within the device, a glow is emitted from the functionalized fullerenes as long as the functionalized fullerenes are isolated from oxygen or another oxidizer. The oxygen free environment can be any non-oxidizing environment such as a non-oxidizing gas, a vacuum, or within an oxygen free matrix which acts as a barrier to diffusion of oxygen to the functionalized fullerenes. The matrix can be any organic solid, inorganic solid, polymer, polymer composite, metal, metal alloy, glass, ceramic, or any combination thereof. The functionalized fullerenes include fullerenes ($C_x$ where x is 20 to 1500) with side groups attached to the fullerene by covalent bonds, ionic bonds, or Dewar coordination, Kubas interactions, or any combination thereof Useful side groups include, but are not restricted to, OH, Br, H, Gd, Ti, or $C(COOH)_2$ groups. Functionalized fullerenes also include substituted fullerenes and endohedral fullerenes. Substituted fullerenes are fullerenes in which one or more of the atoms which comprise the fullerene cage structure are replaced by an atom other than carbon. Endohedral fullerenes have additional atoms, ions, or clusters enclosed within their inner spheres. The irradiated functionalized fullerenes can glow with an output of a distribution of wavelengths and with an emission intensity that depends on the intensity of irradiation. The radiation can be from any part of the electromagnetic spectrum from $10^{-12}$ to $10^{12}$ m in wavelength. The radiation can be of a larger wavelength than the emitted light. The irradiation source can be a laser beam or an incoherent source.

Small amounts of oxygen can cause combustion and the loss of luminescence. In one embodiment of the invention, the sensitivity of the functionalized fullerene to oxygen allows the construction of an oxygen sensor that is highly sensitive. Because oxygen decomposes the functionalized fullerene, oxygen sensing is irreversible. The irreversibility of oxygen promoted decomposition allows for the recording of the history of exposure of a sensor where different portions of the sensor exposed to oxygen containing atmospheres can be irradiated at different times. In another embodiment, the degree to which luminescence is lost in various portions of the sensor can be used to record the level of oxygen in the atmospheres where the sensor is placed. Oxygen levels can be determined by measuring the intensity of the emission of portions when later irradiated in an oxygen free atmosphere to determine the level of oxygen present at various times in the atmosphere.

When functionalized fullerenes are fixed within a thermoplastic such that they are normally shielded from oxygen, the luminescence upon irradiation can be used, according to another embodiment of the invention, to detect any cracks or other defects that would expose the functionalized fullerenes to oxygen. Additionally, the irradiation of the functionalized fullerenes at the defect in the presence of oxygen can be used for the repair of defects. In this embodiment, the combustion of the functionalized fullerene heats the thermoplastic to the point of melting, which upon solidification of the melt after cessation of irradiation or complete loss of the functionalized fullerene reseals the defect. Such a system can be considered an irradiation induced self-healing material.

In another embodiment of the invention where the functionalized fullerene is employed in an oxygen free environment, or has been embedded in a matrix that isolates the functionalized fullerene from oxygen, the luminescence allows the functionalized fullerenes to act as phosphors. These phosphors can be used in a variety of applications. For example, in one embodiment the phosphor can be used as a target for a light beam such as a laser beam. The emitted light can be used as a signal to determine the location of the target. The light emitting target allows for an observation of the target by a detector at any location that has a direct line of sight to the phosphor. In another embodiment of the invention the phosphor can be used as a video display.

DETAILED DESCRIPTION OF THE INVENTION

Figure 1:
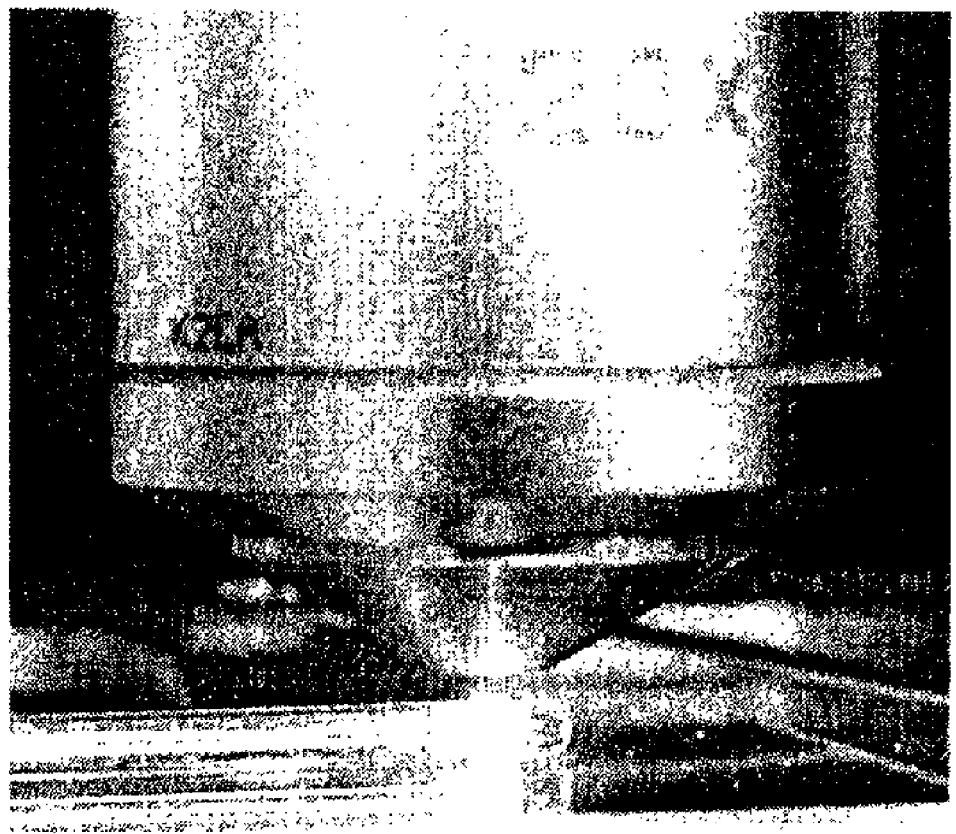
FIG. 1 is a reproduction of a photograph showing optical luminescence of fullerene hydride particles in a vacuum sealed capillary tube excited by a laser beam at 785 nm.

Optical ignition of carbon nanotubes was first disclosed by Ajayan et al. ("Nanotubes in a Flash—Ignition and Reconstruction." *Science*, 2002, 296, 705) where it is disclosed that under vacuum, the carbon nanotubes undergo ignition and reconstruction upon irradiation with light, but this ignition or reconstruction behavior was not observed with fullerenes. The invention was enabled by the Inventor's discovery that functionalized fullerenes could also undergo optical ignition in a manner similar to that observed for carbon nanotubes. It is discovered that a material comprising functionalized fullerenes emits an intense glow upon irradiation with electromagnetic radiation above a threshold intensity in the absence of oxygen or other oxidizing agents, but releases heat and undergoes spontaneous oxidation or combustion when the functionalized fullerenes experience the presence of oxygen, or other oxidizing agents, with loss of emission. Therefore, the subject invention relates to a method of illumination which comprises providing a material comprising functionalized fullerenes and irradiating the material in an oxygen free environment. The optical luminescence of the functionalized fullerenes is dependent on the irradiation intensity. The luminescence can be excited by a host of electromagnetic wavelengths and light of various wavelengths can be emitted. Because oxygen or other oxidizers combust or otherwise oxidatively decompose the functionalized fullerenes, the irradiation step must be performed in an oxygen free environment. Although all subsequent disclosure will refer to oxygen for oxidation or combustion of the functionalized fullerenes, it should be understood that oxygen is an equivalent to other oxidizing agents and, therefore, oxygen free environment can alternately, or additionally, require absence of any other oxidizing agent. The oxygen free environment can be established through any physical and/or chemical technique. In one embodiment, the oxygen free environment can be a vacuum. In another embodiment, the oxygen free environment can be a non-oxidizing gas (e.g., nitrogen, argon) atmosphere.

The term "fullerenes" defines a general class of molecules that exists essentially in the shape of a three dimensional polyhedron containing from 20 to 1500 carbon atoms, and which comprises carbon atoms as the predominant atomic moiety from which they are composed. The fullerenes herein include but are not limited to fullerenes such as C-28, C-32, C-44, C-50, C-58, C-60, C-70, C-84, C-94, C-250 and C-540. (According to this nomenclature, the fullerene which contains 60 carbon atoms is denoted C-60, the fullerene which contains 70 carbon atoms is denoted C-70, etc.) Functionalized fullerenes include fullerenes ($C_x$ where x is 20 to 1500) with side groups attached to the outer surface of the cage via covalent bonds, ionic bonds, or Dewar coordination, or Kubas interactions, or any combination thereof. The side groups can be either inorganic, including, but not exclusive to, OH, Br, $H_2$, Gd, Ti, organic, including, but not exclusive to, $C(COOH)_2$, or any combination of organic and/or inorganic functional groups. The number of functional groups attached per cage of fullerene can vary from 1 to a majority of the number of carbons in the fullerene cage. Also included among the functionalized fullerenes for purposes of the invention are the substituted fullerenes. These are fullerenes in which one or more of the atoms which comprise the fullerene cage structure is replaced by an atom other than carbon, such as nitrogen, boron or titanium, yet essentially retain the geometry of a polyhedron upon being so substituted. Also included among the functionalized fullerenes are endohedral fullerenes in which atoms of elements other than carbon (e.g., iron) reside inside the cage structure. Functionalized fullerenes have different physical and chemical properties based on the type and number of side groups, endohedral elements, and substituted elements. The functionalized fullerenes have dimensions that can be in excess of a nanometer in diameter, and can be considered nanoparticles.

The material comprising functionalized fullerenes can include a matrix to secure, orient, and isolate the fullerenes. In one embodiment the functionalized fullerenes can be adhered or otherwise locked to a surface of the matrix. In another embodiment the functionalized fullerenes can be embedded within the matrix. The matrix can be an organic gas, liquid or solid; an inorganic gas, liquid, or solid; a polymer or polymer composite; water, an aqueous solution or aqueous suspension; a metal or metal alloy; a glass or ceramic; a biological or biologically derived material; or any mixture of these materials. When a polymer is used, the polymer may be a rubber, plastic, or cross-linked resin.

The irradiation source can be any electromagnetic radiation, where the wavelength of the radiation can range from $10^{-12}$ m to $10^{12}$ m, which includes gamma rays, x-rays, extreme ultraviolet, ultraviolet, visible, infrared, microwave, radio wave, or any combination thereof. The irradiation source can be coherent or incoherent, such as a laser beam or a radio wave. As the intensities of radiation increases, the luminescence will increase.

In one embodiment of the subject invention, there is provided a luminescent device comprising a material comprising functionalized fullerenes and an irradiation source. Functionalized fullerenes undergo spontaneous combustion upon electromagnetic irradiation in air; while under an oxygen free environment, the functionalized fullerenes glow until irradiation subsides. The optical sensitivity of functionalized fullerenes to oxygen has enabled them for use in various applications, such as ultra-sensitive oxygen detection, self-healing materials, and space applications. For example, in one embodiment of the invention, a material comprising functionalized fullerenes can be included as an optical sensor for ultra-sensitive detection of oxygen, where diminished or destroyed luminescence from the material indicates the presence of oxygen.

In the oxygen sensing embodiment, functionalized fullerenes can glow upon electromagnetic irradiation when oxygen is absent. Detection of the glow can be at any wavelength or combination of wavelengths within the emitted spectrum including at the wavelength of irradiation. The emission can be visible light and the irradiation can be non-visible. The material comprising functionalized fullerenes can include exclusively functionalized fullerenes or functionalized fullerenes combined with at least one other material. For example the functionalized fullerenes can be dispersed within, or otherwise encased in, an oxygen permeable polymer, metal, glass, or ceramic matrix. The functionalized fullerenes can be dispersed in or covered by a fluid. It is known to those skilled in the art that because of the nanoscale size of functionalized fullerenes, as well as their solubility in polar and non-polar solvents, the terms such as "dissolve," "disperse" and "suspend" can be interchangeable herein, as can be "solution," "dispersion" and "suspension," as in some cases it is not readily apparent that for the liquid phase employed if a true solution or a suspension is formed. In some embodiments of the invention, as is obvious to one skilled in the art, a solution and dispersion are distinct entities. The sensitivity and rate of the response can be augmented by the nature of the matrix or other materials. The sensitivity of the response can also be augmented by the intensity of the irradiation.

In many embodiments, the presence of oxygen diminishes or destroys the functionalized fullerene comprising sensor at the site where irradiation occurs. In an embodiment of the invention for an oxygen sensing material, a light source, such as a laser beam, traverses a surface of a material comprising functionalized fullerenes. By knowing the change in emitted light at the specific irradiation position on the material's surface over time, one can encode a record of the exposure of the material to oxygen over the observed time by a latter emission from the same position on the surface in an oxygen free environment. Furthermore, such a record on the material's surface can be used to cross check with a record of defects of articles that occur in a fabrication line where an oxygen free environment is necessary for the quality of the article.

In another embodiment the novel oxygen sensor can be employed for the detection of oxygen, an important indicator of potential life, in remote locations, such as a planet, moon, artificial satellite, or asteroid of the solar system or can be employed in remote places on earth to which a sensor can be transported. In this manner, a decrease or loss of emission indicates the presence of oxygen.

In another embodiment of the invention, a material comprising functionalized fullerenes can act as a self-healing material where sufficient heat is generated upon irradiation to melt the material, but only in the vicinity of functionalized fullerenes that are exposed to oxygen by a defect. The material near the defect subsequently fuses into a healed material upon cooling after the cessation of irradiation or the consumption of the functionalized fullerenes at the defect. The defect's position can be discovered by the observation of diminishing luminescence in that portion of the material during irradiation. In this embodiment the functionalized fullerene can be fixed within a thermoplastic, including, but not exclusive to, poly(styrene), poly(methyl methacrylate), poly(ethylene), poly(propylene), polycarbonate, poly(ethylene terephthalate), poly(butylene terephthalate), and nylon. The thermoplastic with embedded functionalized fullerenes can be irradiated with a radiation source and display luminescence. In air, or other oxygen containing atmosphere, any defects, such as a crack that exposes functionalized fullerenes to oxygen results in combustion of the functionalized fullerenes upon irradiation. The local heating by combustion provides a sufficient temperature to cause melting of the thermoplastic in the immediate vicinity of the radiation-exposed functionalized fullerenes. Upon cessation of irradiation or complete combustion of the exposed functionalized fullerenes, the thermoplastic melts and subsequently solidifies to seal the defect that exposed the functionalized fullerenes. In this manner, a thermoplastic for use in an environment where an irradiation source exists can act as a radiation promoted "self-healing" material.

In yet another embodiment, the functionalized fullerene comprising material is sealed from air and acts as a phosphor when irradiated. In the specific radiation addressed phosphor embodiment of the invention, a material comprising functionalized fullerenes can be sealed within an oxygen impermeable material, or can be used unsealed if the environment in which the phosphor is present is an oxygen free atmosphere. An intense glow will occur upon irradiation of the material comprising functionalized fullerenes. The irradiation can be from a laser source, such that a well defined light path can be directed to the target phosphor. When the laser beam impinges on the functionalized fullerene within the material, a glow occurs that will have essentially a constant intensity radiating in all directions not blocked by an opaque surface upon which the target phosphor material is attached. In this manner, the location of a remote device can be verified or found when the excited emission is observed with a detector. Such a location system, based on a laser beam induced emission from a target phosphor, allows determination of the phosphor's position using a detector that is either at the source of the laser beam or at any other location in direct line of sight to the target phosphor. Many different detectors can be employed for the practice of the method according to an embodiment of the invention for using a phosphor target to determine a position. Any optical detector known by those skilled in the art can be used.

Alternate remote location targeting methods known in the art involve the reflectance of light from a surface and require that the angle of the surface relative to the light source is within a very small window of angles such that the reflected signal from the target is received by a fixed detector. For example, a detector at the laser beam source would require that the reflective surface be nearly perpendicular to the beam to assure detection. Small rotations of the target can result in no detection even when the reflective target is struck by the laser beam. As the emission from the functionalized fullerenes would emanate in all directions from the target, any detector that has a direct line of site to the target can detect the target. In this manner multiple detectors can be used for a redundant determination of the position. This described location system can even be employed in space applications, where functionalized fullerenes can be used in outer space for detection of objects, such as satellites, from earth.

In one embodiment, the target phosphor can be used in a video display. The video display can use a non-visible laser beam to address a target phosphor in a specific location on the display. The broad spectrum visible light phosphor can transmit light to a specific colored filter to generate a color display. Alternately a functionalized fullerene with a functional group that is a coupled conjugated functionality can emit a specific color and ultimately create ultra high-resolution video displays. The intensity of the laser beam can be varied to control the intensity of the light emitted from the phosphor. The target phosphor can be within an effectively transparent or translucent supporting material. Multiple laser beams can simultaneously address different targeted phosphors. The video display surface can be flat, curved, or have any shape, including but not limited to a sphere, cylinder or cube. The laser beam source can be from within the shape or can be directed from any position relative to the viewer of the display. In some embodiments a three-dimensional or holographic image can be generated. In one embodiment functionalized fullerenes can be employed on a screen for use as a Laser TV, where a scanning laser creates image on the screen where functionalized fullerenes coated on the screen luminesce upon irradiation.

Materials and Methods

Two different types of functionalized fullerenes, a polyhydroxy fullerene, $C_{60}(OH)_x$, where x ranges from 20 to 40, and a fullerene hydride $C_{60}H_x$, where x ranges from 18 to 20, were loaded individually into 1.5×90 mm capillary tubes. The tubes were evacuated using a vacuum pump and were sealed with a flame while the contents were under vacuum. The vacuum sealed tubes containing functionalized fullerenes were irradiated with a laser beam of 785 nm. During irradiation, the functionalized fullerenes glowed until exposure to the laser beam was ceased. FIG. 1 shows the visible emission of a fullerene hydride containing capillary tube upon near IR irradiation with a laser.

Figure 2:
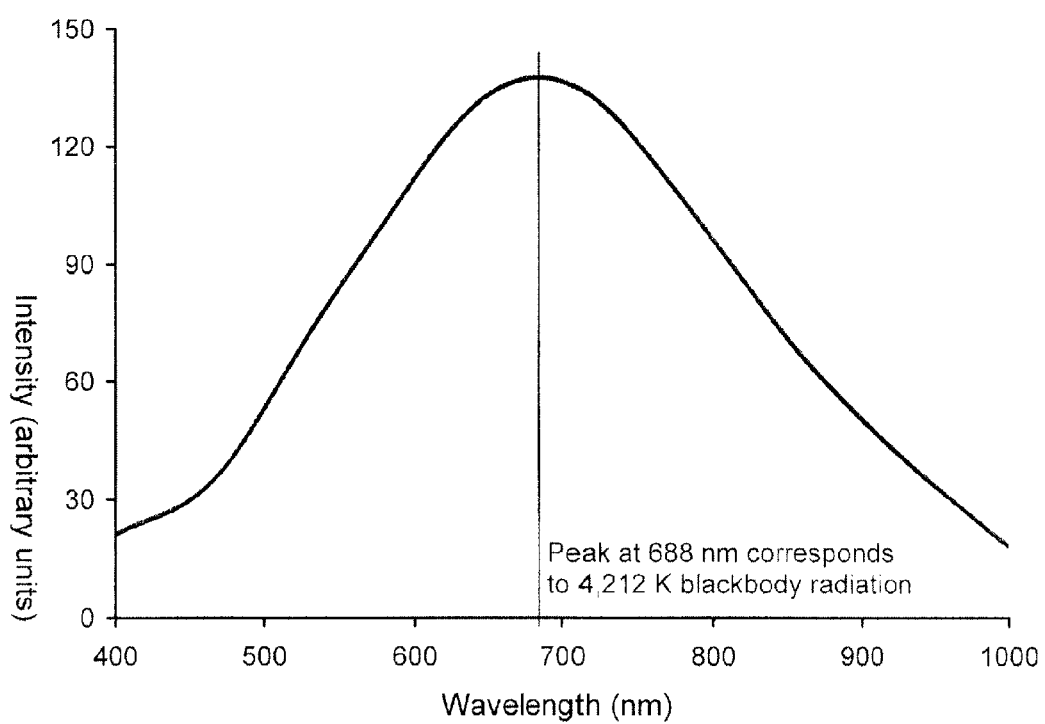
FIG. 2 is an emission spectrum of carboxy fullerenes in vacuum sealed capillary upon irradiation with a laser at 785 nm.
Figure 3:
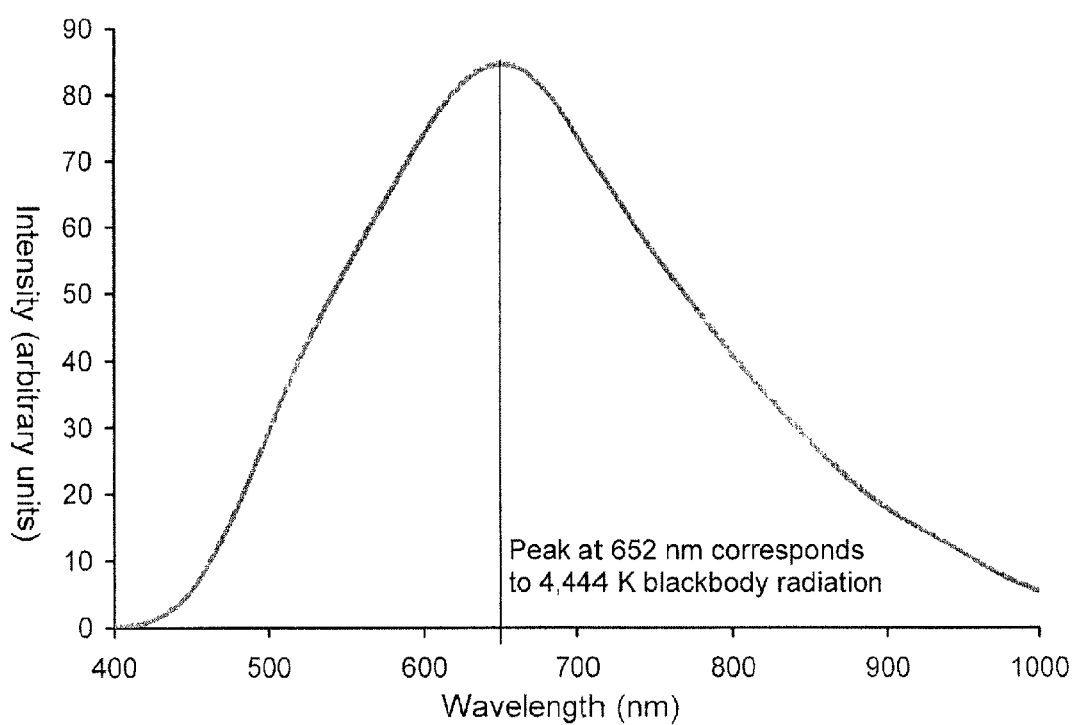
FIG. 3 is an emission spectrum of polyhydroxy fullerenes in vacuum sealed capillary upon irradiation with a laser at 785 nm.

Two different functionalized fullerenes, a polyhydroxy fullerene, $C_{60}(OH)_x$, where x ranges from 20 to 40, and a carboxy fullerene $C_{60}(C(COOH)_2)_3$, were loaded into individual 1.5×90 mm capillary tubes. The tubes were evacuated using a vacuum pump and sealed with a flame while under vacuum. The vacuum sealed tubes containing functionalized fullerenes were irradiated with a laser beam of 785 nm. During irradiation, the functionalized fullerenes glowed until exposure to the laser beam was ceased. The emission spectra of glowing functionalized fullerenes were recorded with USB2000 fiber optic spectrometer (Ocean Optics, Fl., USA). Emission spectra for polyhydroxy fullerenes and carboxy fullerenes are shown in FIGS. 2 and FIG. 3, respectively. The emission spectra are continuous and similar to blackbody radiation spectrum. Reduction in intensity at low (<500 nm) and high (>800 nm) wavelengths is due to reduced sensitivity of the spectrometer in these regions. The peak at 688 nm for carboxy fullerenes and 652 nm for polyhydroxy fullerenes correspond to blackbody temperatures of 4,212 K and 4,444 K, respectively.

All patents, patent applications, provisional applications, and publications referred to or cited herein, supra or infra, are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

We claim:

1. A method of illumination, comprising the steps of:
   providing a material comprising functionalized fullerenes; and
   irradiating said material with an electromagnetic radiation in an oxygen free environment, wherein said material emits light.

2. The method of claim 1, wherein said functionalized fullerenes comprise:
   fullerenes ($C_x$ where x is 20 to 1500) with functional groups attached to said fullerene by covalent bonds, ionic bonds, or Dewar coordination, Kubas interactions, or any combination thereof;
   endohedral fullerenes;
   substituted fullerenes; or
   any combination thereof.

3. The method of claim 2, wherein said functional groups comprise OH, Br, H, Gd, Ti, or $C(COOH)_2$.

4. The material of claim 1, wherein said functionalized fullerenes are dispersed in a matrix or attaching to said matrices' surface.

5. The material of claim 4, wherein said matrix comprises: an organic gas, liquid or solid; an inorganic gas, liquid, or solid; a polymer or polymer composite; water, an aqueous solution or aqueous suspension; a metal or metal alloy; a glass or ceramic; a biological or biologically derived material; or any mixture thereof.

6. The method of claim 1, wherein said electromagnetic radiation ranges from $10^{-12}$ m to $10^{12}$ m in wavelength and comprises gamma rays, X rays, extreme ultraviolet, Ultraviolet, visible, infrared, microwave, radio wave or any combination thereof.

7. The method of claim 1, wherein said oxygen free environment comprises a vacuum or a non-oxidizing gas atmosphere.

8. A luminescent device comprising a material comprising functionalized fullerenes and an irradiation source, wherein said material emits blackbody radiation upon irradiation.

9. The device of claim 8, wherein said irradiation source is a laser beam.

10. The device of claim 8, wherein said functionalized fullerenes upon irradiation with a radiation of sufficient intensity undergo degradation or combustion in the presence of oxygen, wherein said device indicates said presence of oxygen by a decrease in the intensity of said light emission.

11. The device of claim 8, wherein said irradiation source is a laser beam that traverses a surface of said functionalized fullerenes, wherein an intensity of said emission from a portion of said surface upon a subsequent irradiation of said portion in the absence of oxygen indicates said presence of oxygen at said portion when said laser beam traversed said portion.

12. The device of claim 8, wherein said material includes a thermoplastic wherein said combustion of said functionalized fullerene melts said thermoplastic in the vicinity of said irradiation.

13. The device of claim 8, wherein said functionalized fullerenes are embedded in a thermoplastic, wherein a physical defect in said thermoplastic exposes said functionalized fullerenes to oxygen, wherein upon said irradiation melts said thermoplastic in the volume adjacent to said oxygen exposed functionalized fullerenes, and wherein solidification of said thermoplastic upon cessation of irradiation or consumption of said exposed functionalized fullerenes, seals said physical defect.

14. The device of claim 8, wherein said functionalized fullerenes are embedded in a gas impermeable matrix, wherein said luminescent device comprises a radiation activated phosphor.

15. The device of claim 8, wherein said functionalized fullerenes are coated on or embedded within a matrix wherein irradiation of at least a portion of said matrix emits visible light from said irradiated matrix wherein said device functions as a display.

16. A method of sensing oxygen, comprising the steps of:
   providing a material comprising functionalized fullerenes;
   irradiating said material, wherein said functionalized fullerenes in said material emit light as blackbody radiation at an intensity depending on the quantity of oxygen to which said functional fullerenes are exposed; and
   detecting said light emission from said material.

17. The method of claim 16, wherein said step of detecting uses a detector that indicates the intensity of said light emission.

18. A method of radiation induced healing of a plastic, comprising the steps of:
providing a material with a plurality of functionalized fullerenes embedded within a thermoplastic; and
irradiating at least a portion of said thermoplastic, wherein any of said functionalized fullerenes exposed to an oxygen containing atmosphere by a defect melts said thermoplastic in the vicinity of said defect; and
solidifying said melted thermoplastic upon cessation of irradiation or consumption of said functionalized fullerene by combustion.

19. A method of locating a target, comprising the steps of:
providing a target comprising functionalized fullerenes, wherein said functionalized fullerenes are sealed from air;
irradiating said target with a laser beam, wherein said functionalized fullerenes in said target emit light;
detecting said light emission and locating said target using at least one detector.

20. The method of claim 19, wherein said detector is at the source of said laser beam or at any other location in direct line of sight to the target.

* * * * *